United States Patent [19]

Lemaignan

[11] Patent Number: 4,462,260
[45] Date of Patent: Jul. 31, 1984

[54] PROCESS FOR PRODUCING A CRACK IN A TUBE

[75] Inventor: Clément Lemaignan, Voreppe, France

[73] Assignee: Commissariat a l'Energie Atomique, Paris, France

[21] Appl. No.: 439,306

[22] Filed: Nov. 4, 1982

[30] Foreign Application Priority Data

Nov. 19, 1981 [FR] France ................. 81 21692

[51] Int. Cl.³ .............................. G01N 1/28
[52] U.S. Cl. ................................... 73/799
[58] Field of Search ............... 73/799, 808, 810, 813, 73/821

[56] References Cited

U.S. PATENT DOCUMENTS 3,421,365 1/1969 Dean et al. ................ 73/799

OTHER PUBLICATIONS

P. F. Packman et al., "Definition of Fatigue Cracks Through Nondestructive Testing," *J. of Materials*, vol. 4, #3, (Sep. 1969), pp. 666–700.

V. A. Vinokurov et al., "Determining Properties of Pipe Metal During Failure with a Specified Crack Velocity," *Ind. Lab.*, vol. 46, #9, (Sep. 1980), pp. 984–986.

*Primary Examiner*—Anthony V. Ciarlante
*Assistant Examiner*—John E. Chapman, Jr.
*Attorney, Agent, or Firm*—Pearne, Gordon, Sessions, McCoy, Granger & Tilberry

[57] ABSTRACT

The present invention relates to a process for producing a crack in a tube.

The tube is placed in a groove made in a support, a load is applied by means of a plate disposed along a generatrix of the tube in order to start a crack and permit the propagation thereof. Load application is stopped when the crack has reached the desired dimensions.

Application is to the production of faults having a controlled size in a tubular member.

3 Claims, 1 Drawing Figure

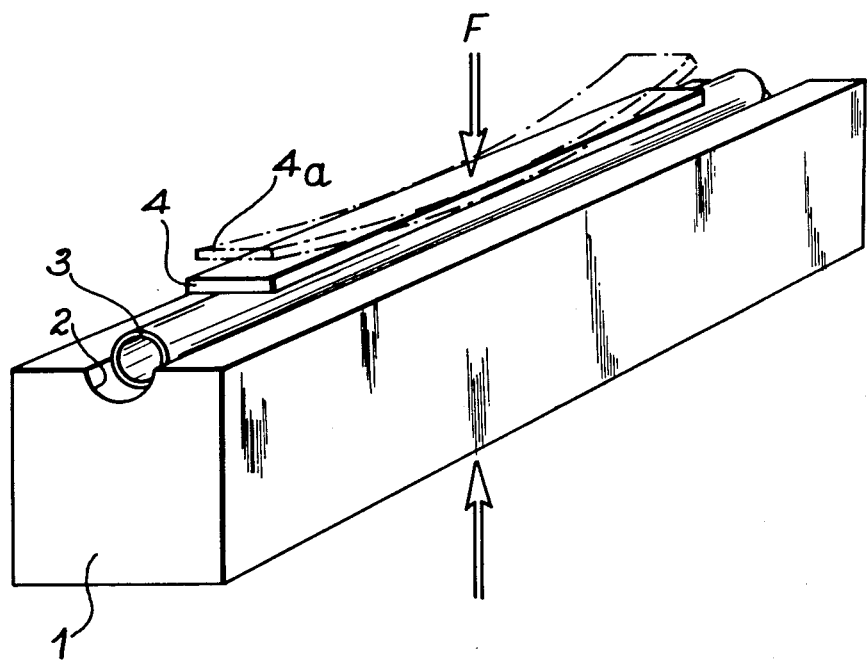

PROCESS FOR PRODUCING A CRACK IN A TUBE

BACKGROUND OF THE INVENTION

The present invention relates to a process for producing a crack, and more particularly a standard crack in a tube.

At present there are numerous inspection methods, which make it possible to investigate faults or defects in tubular members, such as testing by ultrasonics, eddy currents, sweating, etc. In order to permit a calibration of the inspection and testing equipment, artificial faults are produced in standard tube portions. A groove is made for the investigation of longitudinal faults, holes are made for detecting leaks or transverse faults, the dimensions of said grooves or holes being a function of the diameter and thickness of the tubes. A groove or hole only makes it possible to regulate the control equipment and does not constitute an artificial image of the natural fault. Although such an approximation is satisfactory in most industrial applications, there are other fields, particularly the nuclear field, where it is desirable not only to be able to produce the artificial image of a natural fault for calibration purposes, but also to check the size, in the case of simple cracks, or to check the leakage flow rate in the case of a transverse fault.

BRIEF SUMMARY OF THE INVENTION

The present invention relates to a process, which makes it possible to produce faults of given length or leaks with a given flow rate in a tubular member.

According to the main feature of the process according to the invention, it comprises the following stages:
the tube is placed in a groove made in a support and whose shape is adapted to that of the tube in such a way that a generatrix of the tube is in contact with a generatrix of the groove, the radius of curvature of the groove in the vicinity of the generatrix being slightly larger than that of the tube;
a plate is arranged along a generatrix of the tube substantially opposite to the aforementioned generatrix;
the load is applied to the tube via the plate, so as to start a crack;
load application continues, so that the crack can propagate; and
load application is stopped, when the crack has reached the desired dimensions.

As a function of the particular case, the load can be applied in a cyclic manner, in order to produce a fatigue crack, or the tube can be placed in a corrosive environment and the load is then applied continuously in order to produce the crack by corrosion under tension.

DESCRIPTION OF THE DRAWING AND PREFERRED EMBODIMENTS

The invention is described in greater detail hereinafter relative to non-limitative embodiments and the attached drawing, which shows a diagrammatic perspective view of the device used for performing the process according to the invention.

In the drawing it is possible to see a solid support 1 having in its upper part a horizontal groove 2, in which is placed a cylindrical tube 3. Viewed in section, groove 2 is shaped like a semicircle having a slightly larger diameter than the tube. An elongated plate 4 is disposed along the generatrix of the tube opposite to the generatrix along which contact takes place between tube 3 and the bottom of groove 2. This plate transmits to the tube the forces applied by a machine, which can e.g. be a fatigue machine. Following each cycle, the plate deforms and assumes a position 4a shown by broken lines in the drawing. Tube 3 also deforms, but to a greater extent in the area adjacent to plate 4, because groove 2 limits the deformations elsewhere.

If the load applied is adequate, a crack is started after a certain number of cycles, on the inner face of the tube and to the right of the load application point, i.e. where the tensile stresses have their maximum value. On continuing to apply the load, the crack can propagate along the inner face of the tube in the load application zone. As the ends of the tube are free, it is possible to introduce there a detection system making it possible to mark the start of the crack and consequently determine its length. Thus, stress application can be discontinued, when the fault has reached a desired length.

It is also possible to continue to deform the tube until the crack propagates into the thickness thereof and passes to the outside, thus creating a leak. Detection means exist, e.g. control using helium, making it possible not only to detect the presence of a leak, but also to measure the flow rate thereof. Thus, it is possible during load application, to check the advance of the leak and stop the operation when the latter reaches the desired flow rate.

Several ways exist for applying the load in order to start a crack and bring about the propagation of the latter. As described hereinbefore, it is firstly possible to produce a fatigue crack by applying the load in a cyclic manner or by applying the load in a static manner in a corrosive environment. It is thus possible to produce cracks by hydrogen embrittlement or by corrosion under tension by filling the tube with hydrogen or with a suitable corrosive medium.

In the case of a fatigue crack, it is advantageous to work with a constant displacement and not with a constant force. Thus, on calling F the force supplied and D the displacement of that part of the tube to which this force is applied, the compliance, which is the force/displacement ratio $C=(F/d)$ is a function of the crack length.

However, this ratio decreases as the crack propagates, so that on working with constant displacement, force F decreases and the operation is stopped on reaching, for a given displacement d, a value such that the compliance ratio has a value corresponding to the desired length for the crack.

For example, a fatigue machine has been used for precracking zircaloy tubes 4 of external diameter 9.5 mm and internal diameter 8.35 mm, the load being applied via a steel plate of section $1.4 \times 10$ mm. For an ovalization of 170 $\mu$m, corresponding to a load of 610N, a crack started to develop as from 25,000 cycles. After 40,000 cycles it had reached a length of 15 mm.

The process according to the invention has a certain number of particularly interesting advantages. Firstly groove 2 of support 1 has a diameter which is only slightly larger than that of the tube, so that in this way the deformation of the lower part of the latter is limited and the creation of a second crack (whose dimensions would not be controlled) at some other point on the tube is prevented. Moreover, the plate makes it possible to spread the compressive stress and therefore the cracking area. The length of the latter can be varied by varying the strength of the plate. Moreover, the length of the crack is only dependent on the number of cycles and the compliance ratio, it being independent of the plate length. Finally, as the complete tube is in an elastic state throughout the operation, there is no metallurgical modification of the metal outside the area immediately adjacent to the lips of the crack.

The process according to the invention has numerous applications, which cover a number of fields, both in industry and in laboratories. The process makes it possible to artificially produce natural defects of given length in the case of cracks or controlled flow rate in the case of leaks. Thus, standards are produced, whose defects are very similar to the natural defects. Thus, it is possible to prepare in this way precracked tubes for testing their resistance to various stresses and the like, such as corrosion, creep, bursting, etc. It is also possible to produce a local fault in a tube which would serve as a bursting disk.

Finally, although the embodiment described relates to a cylindrical tube, it is obvious that the invention can also be used for producing faults in tubes which do not have a circular cross-section. (e.g. an oval tube), it merely being necessary for this purpose to modify the shape of groove 2. The process according to the invention can be applied to all types of tubes, no matter what their shape and dimensions, even to small diameter tubes.

What is claimed is:

1. A process for producing a crack on the inner face of a tube, wherein it comprises the following stages:
   the tube is placed in a groove made in a support and whose shape is adapted to that of the tube in such a way that a generatrix of the tube is in contact with a generatrix of the groove, the radius of curvature of the groove in the vicinity of the generatrix being slightly larger than that of the tube;
   a plate is arranged along a generatrix of the tube substantially opposite to the aforementioned generatrix;
   a load is applied to the tube via the plate, so as to start a crack;
   load application continues, so that the crack can propagate; and
   load application is stopped, when the crack has reached the desired dimensions.

2. A process according to claim 1, wherein the load is applied cyclically in order to produce a fatigue crack.

3. A process according to claim 1, wherein the tube is placed in a corrosive environment and the load is continuously applied in order to produce the crack by corrosion under tension.

* * * * *